(12) United States Patent
Leath et al.

(10) Patent No.: US 10,932,698 B2
(45) Date of Patent: Mar. 2, 2021

(54) NON-INVASIVE SENSING SYSTEM

(71) Applicant: SENSORFLO LIMITED, Cambridge (NZ)

(72) Inventors: Shane Richard Leath, Huntington Hamilton (NZ); Robin Holdsworth, Huntington Hamilton (NZ)

(73) Assignee: SENSORFLO LIMITED, Cambridge (NZ)

( * ) Notice: Subject to any disclaimer, the term of this patent is extended or adjusted under 35 U.S.C. 154(b) by 190 days.

(21) Appl. No.: 16/065,477

(22) PCT Filed: Dec. 23, 2016

(86) PCT No.: PCT/NZ2016/050209
§ 371 (c)(1),
(2) Date: Jun. 22, 2018

(87) PCT Pub. No.: WO2017/111623
PCT Pub. Date: Jun. 29, 2017

(65) Prior Publication Data
US 2019/0008422 A1    Jan. 10, 2019

(30) Foreign Application Priority Data

Dec. 24, 2015 (NZ) ........................................ 715630

(51) Int. Cl.
*A61B 5/145* (2006.01)
*G01N 22/00* (2006.01)
(Continued)

(52) U.S. Cl.
CPC ............ *A61B 5/145* (2013.01); *A61B 5/0507* (2013.01); *A61B 5/14532* (2013.01);
(Continued)

(58) Field of Classification Search
CPC . A61B 5/145; A61B 5/14532; A61B 5/14546; A61B 5/68; A61B 5/6801; A61B 5/6824; A61B 5/7235
See application file for complete search history.

(56) References Cited

U.S. PATENT DOCUMENTS 8,882,670 B2    11/2014  Hancock
9,198,607 B2 *  12/2015  Fischer ................. A61B 5/145
(Continued)

FOREIGN PATENT DOCUMENTS

EP    1 620 002 B1    2/2006
GB    2 433 603 A     6/2007

OTHER PUBLICATIONS

International Search Report, dated May 29, 2017, from corresponding PCT/NZ2016/050209 application.
(Continued)

*Primary Examiner* — Eric F Winakur
(74) *Attorney, Agent, or Firm* — Nixon & Vanderhye

(57) ABSTRACT

A non-invasive sensing system for measuring the concentration of a substance within an object, the system including a support element adapted to be placed near to, or against, a surface of the object, a first transmitting antenna mounted upon or within the support element for transmitting electromagnetic radiation signals into the object, and a second receiving antenna mounted upon or within the support element, and adjacent to the first transmitting antenna, for receiving at least a portion of the electromagnetic radiation signals that are reflected back to the same surface of the object covered by the support element, due to the transmitted electromagnetic radiation signals having interacted with the substance within the object being measured.

22 Claims, 8 Drawing Sheets

Figure 1:
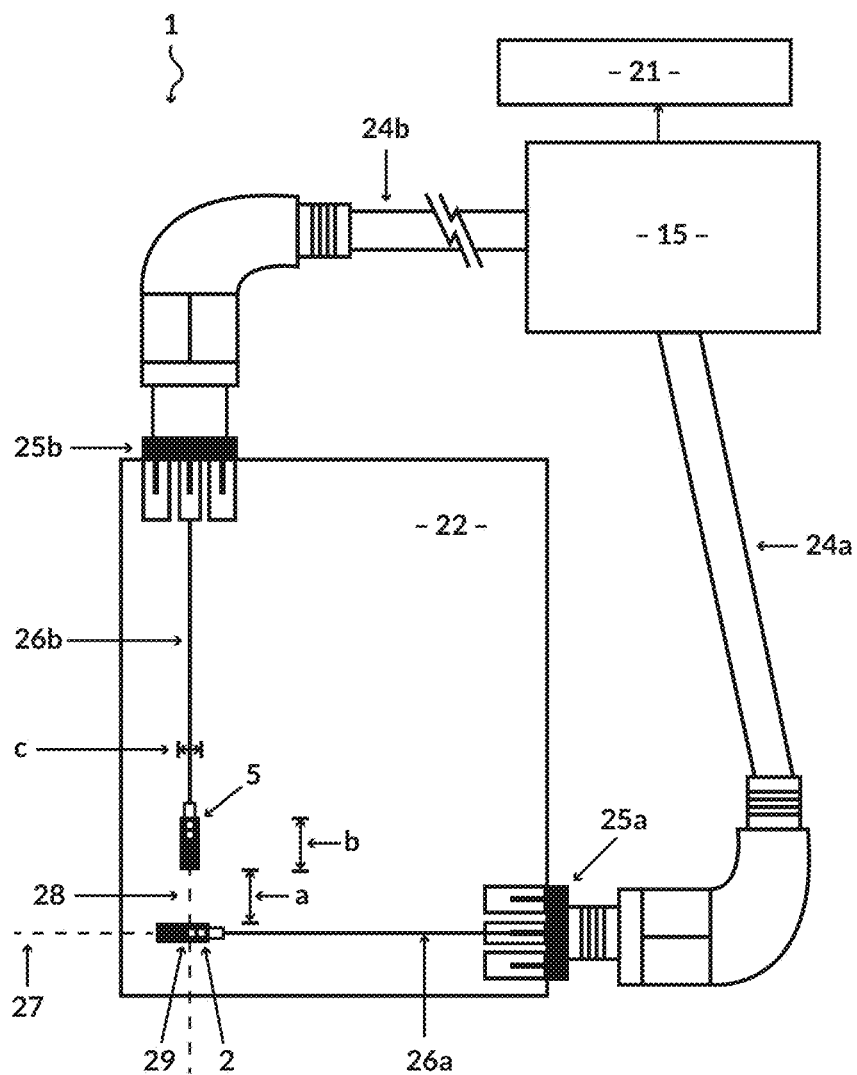

(51) Int. Cl.
 A61B 5/1455 (2006.01)
 A61B 5/00 (2006.01)
 A61B 5/0507 (2021.01)
 G01N 33/49 (2006.01)
(52) U.S. Cl.
 CPC ........ *A61B 5/14552* (2013.01); *A61B 5/6801* (2013.01); *A61B 5/681* (2013.01); *A61B 5/6898* (2013.01); *A61B 5/7235* (2013.01); *G01N 22/00* (2013.01); *G01N 33/49* (2013.01)

(56) References Cited

U.S. PATENT DOCUMENTS

| | | |
|---|---|---|
| 2010/8324398 | 12/2010 | Tzyy-Ping |
| 2012/0130212 A1 | 5/2012 | Pluta et al. |
| 2013/0225960 A1 | 8/2013 | Porch et al. |
| 2013/0289375 A1 | 10/2013 | Fischer |
| 2014/0128702 A1 | 5/2014 | Brister et al. |
| 2014/0142400 A1 | 5/2014 | Halaka |
| 2014/0194715 A1 | 7/2014 | Griswold |
| 2014/0213870 A1 | 7/2014 | Hsu et al. |
| 2015/0045635 A1 | 2/2015 | Tankiewicz et al. |
| 2015/0110721 A1 | 4/2015 | Conrad et al. |
| 2015/0112167 A1 | 4/2015 | Conrad et al. |

OTHER PUBLICATIONS

Suster, M. et al.: "An RF/Microwave Microfluidic Sensor Based on a 3D Capacitive Structure with a Floating Electrode for Miniaturized Dielectric Spectroscopy.", Sensors, 2014, pp. 1784-1787, XP032705258 *.
Liao, Y-T. et al.: "A 3µW Wirelessly Powered CMOS Glucose Sensor for an Active Contact Lens", IEEE International Solid-State Circuits Conference (ISSCC) 2011, Session 2/Technologies for Health/2.3, 2011, pp. 38-40, XP032013628.
Cooke, S. J., S. G. Hinch, et al. (2006). "Mechanistic basis of individual mortality in pacific salmon during spawning migrations." Ecology 87(6): 1575-1586.

* cited by examiner

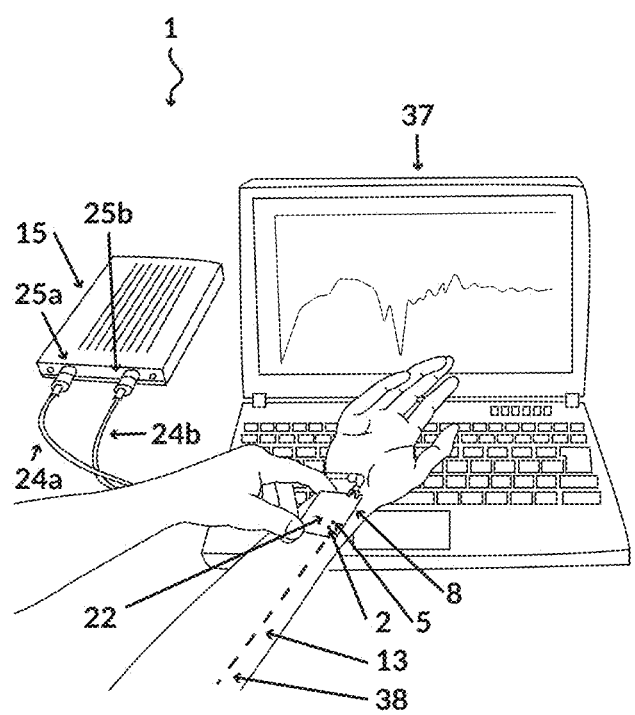
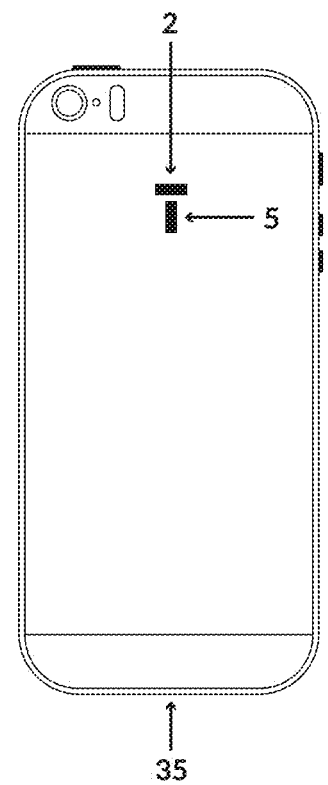
FIG 5
FIG 6

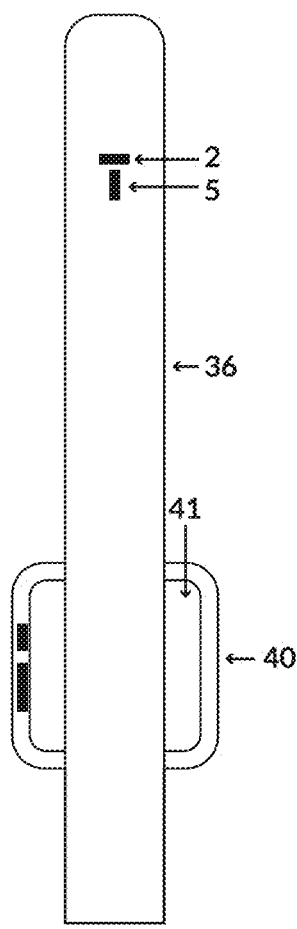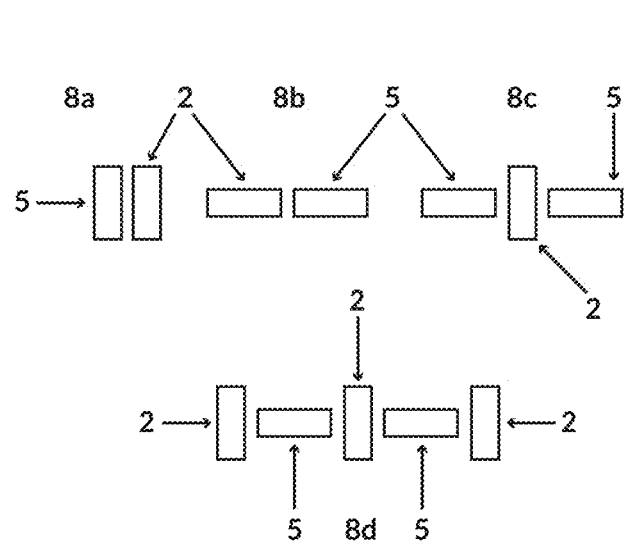
FIG 7
FIG 8

NON-INVASIVE SENSING SYSTEM

FIELD

This invention relates to a non-invasive sensing system.

The invention may be suitable for use in non-invasively detecting the presence of, and/or measuring the concentration(s) of, a substance(s) within an object.

More specifically, the invention may be particularly suitable for use in non-invasively detecting the presence of, and/or measuring the concentration(s) of, a substance within the blood of a living being, for example metabolites, lactate, urates, blood sugar (glucose), water, alcohol, and drugs. For convenience only therefore, the invention will be predominantly described in relation to such use.

However, it is to be understood and appreciated that the invention may also have other applications and/or uses.

The prior art and possible applications of the invention, as discussed below, are therefore given by way of example only.

BACKGROUND

Diabetes mellitus, which is more commonly referred to as diabetes, is a chronic metabolic disease characterised by high blood sugar (glucose) levels over a prolonged period of time. It can also be described as a condition where a person's blood glucose levels cannot be regulated normally by the person's body alone. Diabetes is an incurable condition (except in very specific situations).

There are three main types of diabetes, namely Type 1 diabetes, Type 2 diabetes and gestational diabetes.

Type 1 diabetes is caused by the failure of the pancreas to produce enough insulin.

Type 2 diabetes is a condition which is primarily caused by a person's cells failing to respond properly to insulin (and is primarily, but not exclusively, caused by a person having excess body weight and/or a poor diet and/or not exercising enough).

Gestational diabetes occurs in pregnant woman who have not previously had a history of diabetes.

Generally speaking, if a person undertakes a fasting blood test and records a blood glucose level below 5.5 mmol/l they do not have diabetes. If they record a level between 5.5 mmol/l-6.9 mmol/l they can be said to have impaired fasting glucose, a type of prediabetes—which increases their risk of developing Type 2 diabetes. A level above 6.9 mmol/l usually means the person has diabetes.

Furthermore, if a person had a randomly-timed blood glucose test (rather than a fasting blood test), a blood glucose level above 11.1 mmol/l will usually mean the person has diabetes.

As of 2015, an estimated 400 million people worldwide suffer from diabetes, with approximately 90% of the cases being Type 2 diabetes. This disease is therefore a significant health burden in virtually every country, and also results in a significant number of deaths each year.

The main treatment methods for diabetes include dietary regulation (to optimise blood glucose levels), insulin injections, and oral medications.

The control or management of blood glucose levels requires that a diabetic regularly self-monitor or self-measure their blood glucose levels, and (if or when considered necessary) administer an appropriate amount of insulin (or possibly) consume an appropriate type of food/drink to help restore balance if need be).

Most people with Type 2 diabetes measure their blood glucose levels at least once per day. However, people who use insulin to treat the disease (all Type 1 diabetics and many Type 2 diabetics) usually test their blood glucose levels more frequently, usually between two to ten times per day. The more regular testing is primarily done to determine whether or when a dose of insulin may be required, and/or to test the effectiveness of any prior insulin doses.

For an existing diabetic, the most common method of measuring blood glucose levels is by what is known as the finger-prick test. This is an invasive procedure where a person pricks their finger and a droplet of the resultant blood is applied to a glucose meter—which is a medical device capable of determining the concentration of blood glucose levels from a droplet of blood.

However, there are a number of disadvantages or drawbacks associated with the finger-prick test, and the use of glucose meters.

Firstly, many people are averse to the slight pain involved and/or the sight of blood.

Secondly, given the invasive nature of the procedure, there is always a risk of infection.

Thirdly, the finger-prick test is not always accurate, or consistent, in that measurements can be up to 15% different to actual (or as compared to more accurate laboratory testing).

Fourthly, some people suffer from what is known as "brittle fingers", and this may hinder their ability (or desire) to measure their blood glucose levels as frequently as needed.

Finally, over the long term, the invasive nature of the finger-prick test may result in damage to the finger tissue and/or result in an on-going, general feeling of discomfort in the fingers.

Moreover, the glucose meter only measures the blood glucose levels of the person each time that the person draws blood by pricking their finger. That is, the finger-prick test does not enable the person to continuously monitor their blood glucose levels, over time. Hence, the person is unable to gain more comprehensive knowledge of their blood glucose levels or patterns over time (especially when sleeping). Moreover, any occurrences of hyperglycaemia or hypoglycaemia (and/or possible causes of same), between each discrete finger-prick test, are also not able to be noted or recorded.

As a result of the above disadvantages or drawbacks, it would be advantageous if there was available a non-invasive system for measuring blood glucose levels, and preferably with an option for continuous (or more regular) monitoring.

There is currently a significant amount of interest in being the first to develop a cost-effective, accurate and practical system for the non-invasive (and preferably painless) measurement of blood glucose levels. To date, no such system has become commercially available.

A fairly recent review of the many different non-invasive blood glucose monitoring technologies currently being researched and/or investigated may be found in the medical devices publication *Med Devices (Auckl)* 2012; 5: 45-52.

US 2012/0130212 Pluta et al describes a system for non-invasively measuring blood metabolites of a patient by repeatedly measuring a plurality of electromagnetic impedance readings from both the epidermis layer and the dermis layer of the patient, until a difference between the readings exceeds a certain threshold. An impedance value representing the difference is calculated using an equivalent circuit model and an "individual adjustment factor data" representative of a physiological characteristic of the patient. Subsequently, a blood metabolite level of the patient is determined from the impedance value and a "blood metabolite level algorithm".

However, a drawback or disadvantage associated with Pluta is that the "individual adjustment factor data" and the "blood metabolite level algorithm" is/are specific to a particular patient profile—or to a group of patients with a similar profile. For example, one such group profile may be: "Caucasian women between the ages of 45-50, weighing 120-130 pounds, with 15-18% body fat". When a patient falls within this profile, a blood glucose level may be determined using an impedance value representing the difference between the actual readings (epidermis and dermis) and a glucose algorithm tailored to that patient's profile. Pluta also describes a preferred embodiment whereby the glucose algorithm is tailored to each and every patient. Hence, the system in Pluta is somewhat impractical or laborious as it requires each patient to firstly undergo pre-testing for fat content, as well as being asked about their age and weight—before the system can be used to determine that patient's specific blood glucose reading.

Moreover, because Pluta allows for ranges to exist in the pre-tests (eg, the range of 15-18% body fat or 45-50 years of age), the final determination of blood glucose levels will not always be accurate for each patient within these ranges. For example, a woman who was 45 years old, weighing 120 pounds and with 15% body fat would receive the same glucose algorithm as a woman who was 50 years old, weighing 130 pounds and with 18% body fat. Given the importance of accurate blood glucose readings, this is clearly unsatisfactory.

US 2013/0225960 Porch describes a blood glucose monitor for the non-invasive, in-vivo characterisation of a blood glucose level in a living body. The monitor includes a microwave resonator (actually a resonant cavity) having a resonant response to input microwaves and designed so that the response will experience a perturbation by a living body in proximity or contact with the resonator. The monitor also includes detection means for detecting changes in the resonant response from which the blood glucose level can be determined or characterised.

One possible drawback associated with Porch is that the microwave resonator has to be built to pick out the frequency(ies) that correlate to the target and would therefore likely require a difference resonator for each chemical targeted.

U.S. Pat. No. 8,882,670 Hancock describes an apparatus for the (minimally) non-invasive measurement of constituents contained within a biological tissue structure (one example being blood glucose levels). Hancock includes a microwave energy source, a first antenna coupled to the microwave energy source for transmitting microwaves into the tissue structure, and a second antenna arranged for receiving the transmitted microwaves after they have passed through the tissue structure. Hancock also includes a signal processor for determining the resonant frequency of the received microwaves and a data processor arranged to provide an output of the concentration of constituents within the tissue structure according to the determined resonant frequency.

Hancock has a similar disadvantage to Pluta in that certain pre-testing of the individual must be made. Namely, before measurement for an individual can be made, it is necessary to know the thickness of the tissue structure. That is, since there will be a variation in the thickness of the biological tissue structure between individuals (and differences in the composition of the tissue structure, eg, thickness of skin, muscle and fat layers), the resonant frequency of the tissue structure for any given constituent concentration will vary from individual to individual.

A further disadvantage associated with Hancock is that the microwaves have to pass through a significant thickness of tissue (eg, through an entire human arm or wrist) before they are received by the second antenna. Moreover, the microwaves have to pass through several layers of different types of tissue (eg, skin, muscle and fat). Since each tissue layer causes its own unique interactions with the microwaves (eg, in relation to attenuation and phase) the apparatus has to de-convolve these effects. This would be impossible without knowing the thickness of each tissue layer (and hence, without knowing the distance the microwaves have to travel through each tissue layer).

EP 1620002 Esenaliev describes a non-invasive system for determining blood glucose levels in a patient which includes an optical probe with a tip designed to be placed over a vein on the underside of the patient's tongue. The tip of the probe includes an excitation port through which an input signal generated by a signal generator subsystem impinges on a surface of the tissue over the vein, and a response port through which a response signal is received by and forwarded to a detector and analyser—which then converts the response signal into a concentration of a blood component and/or a value of a blood parameter. Esenaliev preferably requires a static magnetic or electrical field.

US 2014/0213870 Hsu et al describes a non-invasive blood glucose monitoring sensor for measuring a numerical value of the blood glucose in a human body by way of placing the non-invasive blood glucose sensor near the human body. The sensor includes a substrate, a first metal layer formed on one surface of the substrate and which includes an internal microstrip antenna, and a second metal layer formed on an opposite surface of the substrate. The sensor further includes a blood glucose sensing unit electrically connected to the first metal layer and the second metal layer and capable of providing an RF signal, wherein the blood glucose sensing unit would output the RF signal to the first metal layer. Therefore, it is claimed, a resonance is produced by the first metal layer with the RF signal and blood glucose in the human body. The numerical value of the blood glucose is allegedly calculated and displayed by the blood glucose sensing unit. Opposite to the substrate, an overlapping area and a non-overlapping area are provided between the first metal layer and the second metal layer for allegedly improving the bandwidth of the microstrip antenna and the sensing sensitivity of the blood glucose sensing unit.

U.S. Pat. No. 9,198,607 Fischer describes an armband that may be fitted to a person's arm. The armband includes a detection device for detecting a blood picture parameter of blood in a blood vessel of the arm and a setting device for setting a predetermined contact pressure of the armband on the arm. The detection device comprises a transmitter configured to transmit a wave signal into the person's arm, and a receiver configured to receive the signal after it has passed through a blood vessel. The setting device is configured in such a way that it can set the predetermined or prescribed contact pressure, at least during the detection of the blood picture parameter by the detection device.

Fischer has a similar disadvantage as Hancock in that the transmitted wave signal has to pass through a significant thickness of tissue (eg, through an entire human arm) before the wave signal is received by the receiver. Fischer also requires pressure to be applied to the arm, via the arm band, and this may be an uncomfortable experience for some people.

US 2010/0324398 Tzyy-Ping is a difficult read, but appears to describe a non-invasive blood glucose monitor which uses "RF impedance data" to determine blood glucose levels.

Cooke, S. J., S. G. Hinch, et al. (2006). "Mechanistic basis of individual mortality in pacific salmon during spawning migrations." *Ecology* 87(6): 1575-1586.

The above article describes the use of a Distell Fatometer which uses a microwave microstrip sensor to measure the water content and then a calibration (for each species of fish) is used to estimate the fat content of the fish. So Fat=factor× water.

However, the results, as described, appear to be fairly unreliable. Furthermore, they are measuring only one component (water) that has the biggest effect, and the measurements take place in the flesh of the fish. By inference they are also saying that they can't measure a second (and only slightly subtler) component. The system is handheld and manually operated.

Object

It is an object of the present invention to provide a non-invasive sensing system which goes some way towards addressing the aforementioned problems or difficulties, or which at the very least provides the public with a useful choice.

Definitions

Throughout this specification unless the text requires otherwise, the word 'comprise' and variations such as 'comprising' or 'comprises' will be understood to imply the inclusion of a stated integer or step or group of integers or steps but not the exclusion of any other integer or step or group of integers or steps.

Statements of Invention

According to one aspect of the present invention, there is provided a non-invasive sensing system for measuring the concentration of a substance within an object, said system including:
  a. a support means adapted to be placed near to, or against, a surface of the object,
  b. a first transmitting antenna mounted upon or within the support means for transmitting electromagnetic radiation signals into the object,
  c. a second receiving antenna mounted upon or within the support means, and adjacent to the first transmitting antenna, for receiving at least a portion of the electromagnetic radiation signals that are reflected back to the same surface of the object covered by the support means, due to the transmitted electromagnetic radiation signals having interacted with the substance within the object being measured.

According to another aspect of the present invention, there is provided a non-invasive sensing system for measuring the concentration of a substance within an object, substantially as described above, wherein the system further includes an analyser which is in electrical communication with the first transmitting antenna and the second receiving antenna, the analyser being adapted to break down the reflected signal received by the second receiving antenna into spectra or a spectral file.

According to another aspect of the present invention, there is provided a non-invasive sensing system for measuring the concentration of a substance within an object, substantially as described above, wherein the system further includes a data processor adapted to receive the spectra or spectral file from the analyser, and turn the reading into a measurement of the concentration of the substance within the object.

According to another aspect of the present invention, there is provided a non-invasive sensing system for measuring the concentration of a substance within an object, substantially as described above, wherein the longitudinal axis of the first transmitting antenna is substantially orthogonal to the longitudinal axis of the second receiving antenna.

According to another aspect of the present invention, there is provided a non-invasive sensing system for measuring the concentration of a substance within an object, substantially as described above, wherein the polarity (or axis of polarity) of the first transmitting antenna is substantially orthogonal to the polarity (or axis of polarity) of the second receiving antenna.

According to another aspect of the present invention, there is provided a non-invasive sensing system for measuring the concentration of a substance within an object, substantially as described above, wherein the central longitudinal axis of the second receiving antenna passes substantially through the midpoint of the first transmitting antenna, or vice versa.

According to another aspect of the present invention, there is provided a non-invasive sensing system for measuring the concentration of a substance within an object, substantially as described above, wherein the centre of the axis of polarity of the second receiving antenna may pass substantially through the midpoint of the first transmitting antenna, or vice versa.

According to another aspect of the present invention, there is provided a non-invasive sensing system for measuring the concentration of a substance within an object, substantially as described above, wherein the support means includes a first conductive track(s) for electrically connecting the analyser to the first transmitting antenna, and a second conductive track(s) for electrically connecting the analyser to the second receiving antenna, wherein the first conductive track(s) is substantially orthogonal to the second conductive track(s).

According to another aspect of the present invention, there is provided a non-invasive sensing system for measuring the concentration of a substance within an object, substantially as described above, wherein the analyser is a vector network analyser (VNA), and the VNA uses S parameters to break down the received signal from the second receiving antenna into spectra or a spectral file.

According to another aspect of the present invention, there is provided a non-invasive sensing system for measuring the concentration of a substance within an object, substantially as described above, wherein, in use, the first transmitting antenna and second receiving antenna are in direct contact with the surface of the object.

According to another aspect of the present invention, there is provided a non-invasive sensing system for measuring the concentration of a substance within an object, substantially as described above, wherein the substance being measured is a blood component within the blood of a body of a living being.

According to another aspect of the present invention, there is provided a non-invasive sensing system for measuring the concentration of a substance within an object, substantially as described above, wherein the transmitted electromagnetic radiation signals are transmitted continuously.

According to another aspect of the present invention, there is provided a non-invasive sensing system for measuring the concentration of a substance within an object, substantially as described above, wherein the transmitted electromagnetic radiation signals are transmitted in pulses or chirps.

According to another aspect of the present invention, there is provided a non-invasive sensing system for measuring the concentration of a substance within an object, substantially as described above, wherein the support means includes a printed circuit board.

According to another aspect of the present invention, there is provided a non-invasive sensing system for measuring the concentration of a substance within an object, substantially as described above, wherein the system is able, or adapted, to operate automatically at predetermined times.

According to another aspect of the present invention, there is provided a non-invasive sensing system for measuring the concentration of a substance within an object, substantially as described above, wherein the system is able, or adapted, to operate automatically and continuously.

According to another aspect of the present invention, there is provided a non-invasive sensing system for measuring the concentration of a substance within an object, substantially as described above, wherein the system is able, or adapted, to be operated manually by a user of the system.

According to another aspect of the present invention, there is provided a non-invasive sensing system for measuring the concentration of a substance within an object, substantially as described above, wherein the system is able to measure the concentrations of a plurality of substances at any one time.

It is to be understood and appreciated that the system may also be used to merely detect the presence of a substance within an object, rather than measure the concentration of the substance within the object.

Accordingly, and according to another aspect of the present invention, there is provided a non-invasive sensing system for detecting the presence of a substance within an object, said system including:
  a. a support means adapted to be placed near to, or against, a surface of the object,
  b. at least one first transmitting antenna mounted upon or within the support means for transmitting electromagnetic radiation signals into the object,
  c. at least one second receiving antenna mounted upon or within the support means, and adjacent to the first transmitting antenna, for receiving at least a portion of the electromagnetic radiation signals that are reflected back to the same surface of the object covered by the support means, due to the transmitted electromagnetic radiation signals having interacted with the substance within the object being detected.

According to another aspect of the present invention, there is provided a method for detecting the presence of, and/or measuring the concentration of, a substance within an object, said method including the step of utilising the non-invasive sensing system, substantially as described above.

For convenience only, the invention will be predominantly described in relation to measuring the concentration of a substance within an object, rather than merely detecting the substance. However, it will be appreciated that if the system can measure the concentration of a substance within an object, then it is of course also detecting that substance within the object. Hence, the invention, as described hereinafter applies to both embodiments of, or uses for, the invention.

The analyser may include a signal generator adapted to facilitate the generation of the electromagnetic radiation signals transmitted by the first transmitting antenna (hereinafter: "first antenna").

The reflected electromagnetic radiation signals received (directly or indirectly) by the analyser from the second receiving antenna (hereinafter: "second antenna") may be analysed by the analyser (or broken down into spectra or a spectral file) utilising techniques such as S Parameters ($S_{11}$, $S_{12}$, $S_{21}$, and/or $S_{22}$) and/or Transmission Line Parameters (Power Loss, Phase angle, RGLC) and/or dielectric parameters ($\Sigma r$, $\Sigma r'$, $\Sigma r''$).

In one embodiment, the analyser may be a VNA.

Other examples of suitable analysers include a voltage standing wave ratio meter (VSWR) or a vector volt meter.

The data processor may comprise or include one or more software program(s) and/or algorithm(s) and/or formulae for transforming the spectra or spectral file received from the analyser into a measurement of the concentration of the substance within the object being measured.

Any suitable support means may be utilised, according to the intended use of the sensing system.

Preferably, the support means may be in the form of, or include, a housing and/or a substrate, upon (or within) which the first antenna and second antenna (and any other electronics or components) may be mounted. Examples of suitable support means (and/or housings/substrates) will be described throughout this specification.

According to another aspect of the present invention, there is provided a non-invasive sensing system for measuring the concentration of a substance within an object, substantially as described above, wherein the system further includes an electronics control module (ECM) for controlling the overall operation of the system and/or the analyser and/or the data processor.

The ECM may be a stand alone unit or it may comprise part of another component of the system, for example the analyser or data processor.

In an alternative embodiment, the data analyser may be included as part of the ECM.

In one embodiment, the electromagnetic radiation signals may include signals that are in the microwave spectrum.

In another embodiment, the electromagnetic radiation signals may include signals that are in the radio wave spectrum.

It is also envisaged that other types of electromagnetic signals may be utilised.

In one embodiment, the electromagnetic radiation signals may include signals from two or more spectra.

In one embodiment, the electromagnetic signals may be transmitted continuously.

In another embodiment, the electromagnetic signals may be transmitted in pulses or chirps.

In one embodiment, the power of the transmitted electromagnetic radiation signals may be below 500 mW, and preferably below 50 mW.

Any suitable type or shape of antennae may be utilised. Examples of suitable antennae may include SMD antennae, wire antennae, travelling wave antennae, reflector antennae, microstrip antennae, log-periodic antennae, and aperture antennae.

In one embodiment, the system may include at least one first transmitting antenna and/or at least one second receiving antenna.

For example, there may be two transmitting antennae and three receiving antennae; or four transmitting antenna and four receiving antennae; or one transmitting antenna and two receiving antennae.

In another embodiment, a plurality of first antennae may be grouped substantially together as one first antenna unit. Likewise, a plurality of second antennae may also be all grouped substantially together as one second antenna unit. Having a plurality of transmitting and receiving antennae within the overall first antenna unit and the second antenna unit may help to ensure that there is always at least one transmitting antenna and at least one receiving antenna above the substance being measured within the object, for example above an artery/vein of a human being if a blood component is the substance being measured.

Hence, the term "first antenna" as used herein shall be understood to also include reference to at least one first transmitting antenna, and/or a first antenna unit, substantially as described above.

Furthermore, the term "second antenna" as used herein shall be understood to also include reference to at least one second receiving antenna, and/or a second antenna unit, substantially as described above.

In one embodiment, the first antenna and the second antenna may be located directly adjacent to each other on the support means.

In such an embodiment, it may be appreciated that the reflected electromagnetic radiation signals (received by the second antenna) are received in substantially the same place and on the same side of the surface of the object, as where the transmitted radiation signals were originally transmitted into the object by the first antenna.

The distance between the first antenna and second antenna may, for example, be between 0.01 mm to 10 cm, but preferably between 0.5 mm to 10 mm In one embodiment, the first antenna and the second antenna may lie in substantially the same plane with respect to each other.

In an alternative embodiment, the first antenna and the second antenna may lie in, or on, different planes.

In one embodiment, the first antenna and the second antenna may be substantially parallel with respect to each other.

In another embodiment, the first antenna and the second antenna may be angled with respect to each other.

In such an embodiment, the first antenna and the second antenna may be angled with respect to each other in substantially the same plane or in different planes (namely, different three dimensional planes or configurations).

Preferably, the first and/or second antennae may be substantially rectangular in shape.

In a preferred embodiment, the longitudinal axis of the first antenna may be substantially orthogonal to the longitudinal axis of the second antenna.

In such an embodiment, the central longitudinal axis of the second antenna may preferably pass substantially through the midpoint (meaning the centre or central region) of the first transmitting antenna, or vice versa.

It will be understood and appreciated that if the first and/or second antennae do not have a clearly defined longitudinal axis (for example, a square, round or hexagonal antenna) the arrangement may be such that the polarity (or axis of polarity) of the first transmitting antenna may be substantially orthogonal to the polarity (or axis of polarity) of the second receiving antenna.

In such an embodiment, the centre of the axis (or central axis) of polarity of the second receiving antenna may pass substantially through the midpoint (meaning the centre or central region) of the first transmitting antenna, or vice versa.

In one embodiment, the first antenna and the second antenna may be embedded within, and enclosed by, the support means.

In another embodiment, the first antenna and the second antenna may lie on the surface of, and/or protrude from, the support means whereby, in use, the first antenna and the second antenna may be in direct contact with the surface of the object.

In such an embodiment, but when used alternatively, one side of the support means may be in direct contact with the surface of the object, with the first antenna and the second antenna lying on, or protruding from, the opposite side of the support means.

In another embodiment, and in use, the support means and/or the first and second antenna may be adapted to be held just above the surface of the object.

In one embodiment, the electromagnetic radiation signals that are transmitted into the object, and the electromagnetic signals that are received back from within the object, may describe or follow a transflectance-type arrangement or pattern.

For convenience only, and throughout this specification, the term "reflected" is to be understood and appreciated as including reflected and transflected electromagnetic radiation signals.

It may be appreciated that the reflected electromagnetic radiation signals that are received by the second antenna have not passed entirely through the object, but instead they have merely passed slightly in and out of the object, with the points of entry (where they are transmitted) and the points of exit (where they are received) being substantially in the same place, and on the same side, of the (surface of) the object.

It is to be understood and appreciated however that only a portion of the electromagnetic radiation signals transmitted into the object by the first antenna will be reflected back towards the second receiving antenna. That is, a portion of the electromagnetic radiation signals transmitted into the object by the first antenna will simply pass through, and/or be absorbed by, the object.

In one embodiment, the support means may include a printed circuit board (PCB).

In one embodiment, the support means may include, or be in the form of, an adhesive patch which may be (temporarily) attached or adhered to the object.

In one embodiment, the substance being measured may be a blood component within the blood of a body of a living being. For example, the system may be used to measure the concentration of glucose or lactate within the blood of a human being.

In such an embodiment, the support means may be adapted, or be able, to be worn by a human being.

In such embodiment, and for example, the support means may be in the form of a strap which may be worn around the waist, arm, leg, neck, ankle or wrist of the human being.

In another embodiment, the system, and/or the support means, may be in the form of, or incorporated within, a smartphone.

In yet another embodiment, the system and/or the support means may be in the form of, or incorporated within, a watch (or medical device) adapted to be continuously worn by a human being.

In one embodiment, or use, the system and/or support means may simply be placed near to, or directly adjacent to, the surface of the object, in order to take a reading.

In an alternative embodiment, or use, the system and/or support means may be placed against the surface of the object, in order to take a reading.

In one embodiment, the system may be able, or adapted, to operate automatically at predetermined times. For example, the system may be configured to automatically take a measurement every hour, 24 hours a day.

In another embodiment, the system may be able, or adapted, to operate automatically and (more-or-less) continuously. For example, the system may be configured to automatically take a measurement every second or every minute, 24 hours a day.

In another embodiment, the system may be able, or adapted, to be operated manually by a user of the system, and at whatever time(s) they decide or see fit to utilise the system.

In such an embodiment, if the system and/or the support means is attached to the object (or worn by a human being) then a user may (for example) manually operate the system by pushing an "on" button associated with the system.

If the system and/or support means is not attached to the object (or worn by a human being) then a user may manually operate the system by bringing the support means adjacent to (or placing it upon) the surface of the object (and optionally pushing an "on" button if the system is not otherwise configured to automatically take a measurement).

In one embodiment, the system may be able to measure the concentrations of a plurality of substances at any one time.

In one embodiment, the system may be able to communicate with an alarm means.

In such an embodiment, and for example, an audible alarm may be associated with the system, or an audible alarm may be associated with an electronic device such a smartphone to which the system has sent an appropriate signal—in the latter example, a text or email could additionally or alternatively be generated and sent.

In such an embodiment, a component of the system (eg ECM or data processor) may send a signal to activate the alarm when a predetermined condition is met (or not met). For example, the alarm may be activated if an impurity, organism or contaminant was detected in a pipeline of milk (or milk powder) or if a person's blood glucose or lactate levels were dangerously low or high.

Preferably, the system may further include power means for powering the operation of the system as a whole, for example for powering the analyser and/or the data processor and/or the ECM and/or the first antenna and second antennae and/or alarm (if housed within the system).

In one embodiment, the power means may be a small battery incorporated within the system, or a component of the system. The battery may be disposable or rechargeable.

The system, or any component thereof, may also include suitable power means to enable it to be powered by mains power, for example by an electrical plug or USB port/cable.

The system may include a communication means, for the transmission of any or all measurements or other data, or any workings on the measurements or other data, to another location, such as a computing system or other electronic device.

The communication means may also be able to receive data, of any kind.

The communications means may be a wireless communication means, for example, a wireless transceiver housed within the ECM or analyser or data processor.

Any suitable wireless technology known in the art may be used, including Wi-Fi (IEEE 802.11), LE Bluetooth®, Bluetooth®, other radio frequencies, Infra-Red (IR), GSM, CDMA, GPRS, 3G, 4G, W-CDMA, EDGE or DCDMA200 and similar technologies.

Alternatively, any suitable wired connections or ports may also be used, including, without limitation, USB ports or any other relevant or appropriate technology known in the art.

The computing device or other electronic system or device (external to the sensing system) may include, without limitation, a mobile phone, a smartphone, an iPhone, an iPad, a tablet, a palmtop computer, a band or other wearable technology device, a small portable device, a laptop, a desktop computer, a cloud computing system, a remote network computer system (a public network, e.g. a website, or alternatively a private network) or to a web service.

The system may be configured to activate the communication means to transfer (and/or receive) measurements or any other data to/from a computing system or other electronic device (external to the system) as or when required or desired. For example, the transmissions may be made in real time, manually, continuously or automatically at predetermined set times.

In some embodiments, the system, or any component thereof, may be configured to receive information or data, of any kind, from another location and/or computer system or electronic devices external to the system, using the communication means. For example, software updates for the antennae, ECM, analyser or data processor may be transmitted in this way.

In one embodiment, the system may be paired with a smartphone loaded with a specific and dedicated software application which allows the smart phone to receive, access, process, display, transmit and/or present the measurements or the data collected by the system.

In such an embodiment, and for example, the analyser may transmit (via the communication means) the spectra or spectral file to the smartphone app, and the smartphone app may therefore act as the data processor in order to turn the received data into an appropriate measurement (of the concentration of the substance being measured within the object).

In another embodiment, the smartphone app may be configured to simply receive (via the communication means) the reflected electromagnetic radiation signals from the second antenna before transmitting them to a remote analyser and/or data processor.

The system, or any component thereof, may include a memory or data storage means for the storage of measurements or any other data.

Alternatively, the memory or data storage means may be housed within a computing system or other electronic device which is in communication with the system.

The system may further include a user interface.

Alternatively, the user interface may comprise part of a computing system or other electronic device which is in communication with the system.

It is envisaged that the system may be utilised for detecting and/or measuring the concentration(s) of any type of substance(s) in any type of object.

That is, the system may be adapted or able to be used for non-invasively detecting the presence of, and/or measuring the concentration(s) of, any type of element, molecule, body, biological tissue, organism, impurity, contaminant, chemical or other substance in any type of body, material, substance, matter or other object (living or otherwise).

It is envisaged however that the system may be particularly suitable for measuring the concentration of metabolites, or any other substances, in the blood of a living being such as a human or animal. For example, the system may be used for measuring the concentrations of substances in the blood of a human being, such as lactate, urates, blood sugar (glucose), water, alcohol, drugs, and so on.

Preferred Embodiments

The description of a preferred form of the invention to be provided herein, with reference to the accompanying drawing, is given purely by way of example and is not to be taken in any way as limiting the scope or extent of the invention.

DRAWINGS

Figure 2:
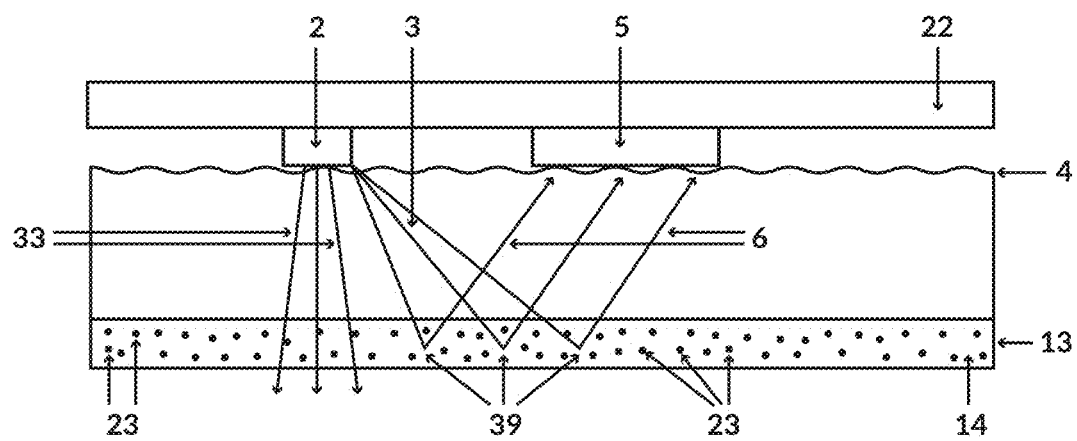
Figure 3:
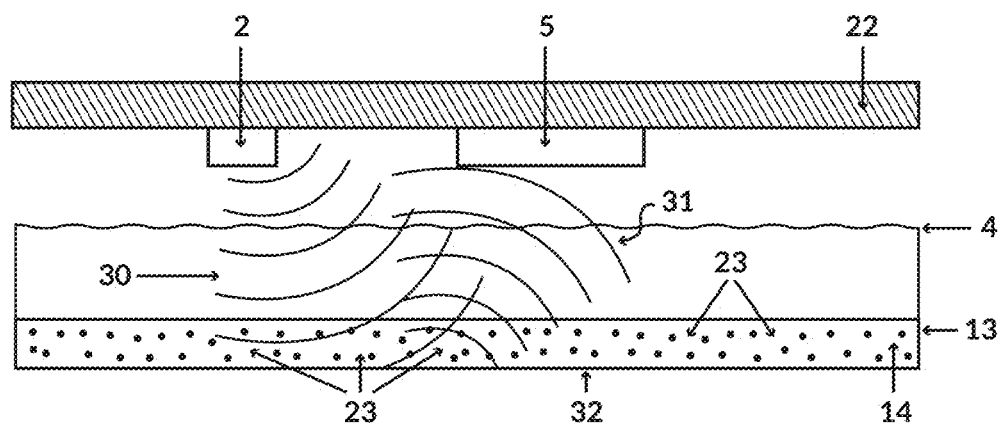
Figure 4:
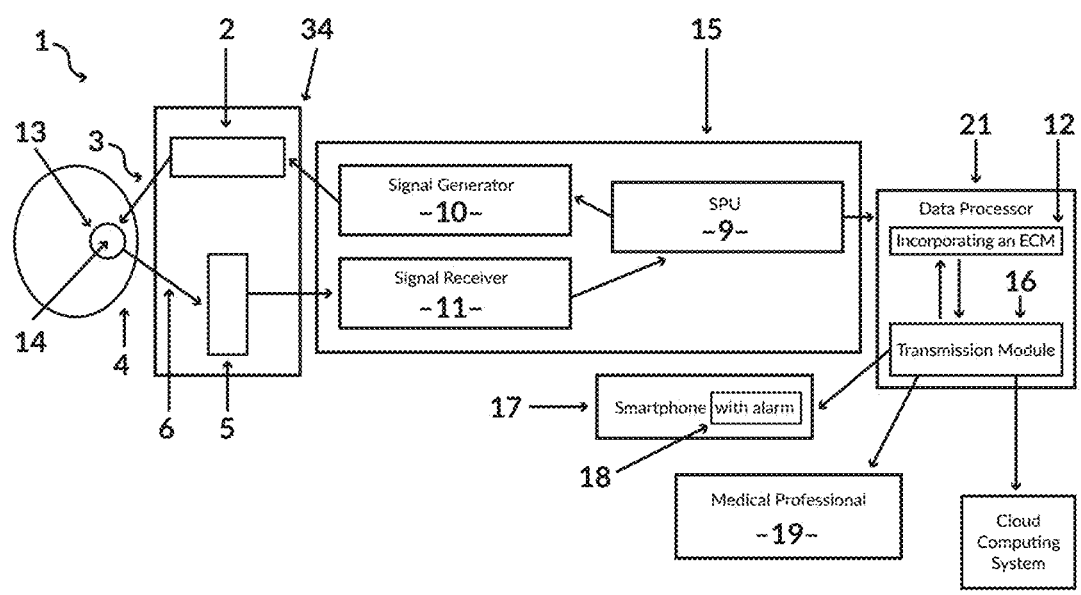
Figure 9:
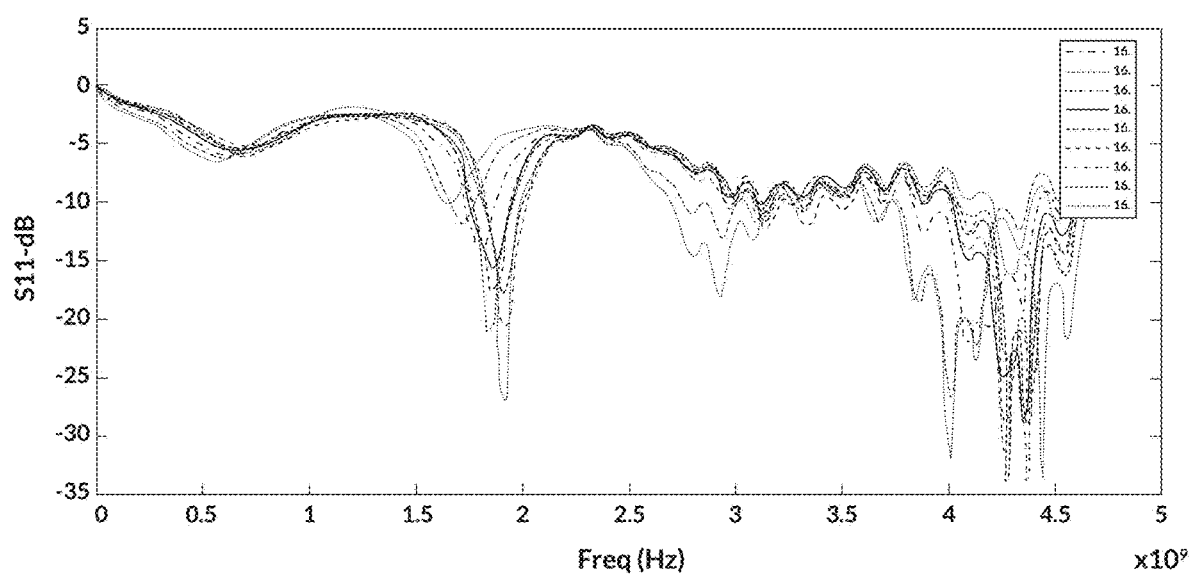
Figure 10:
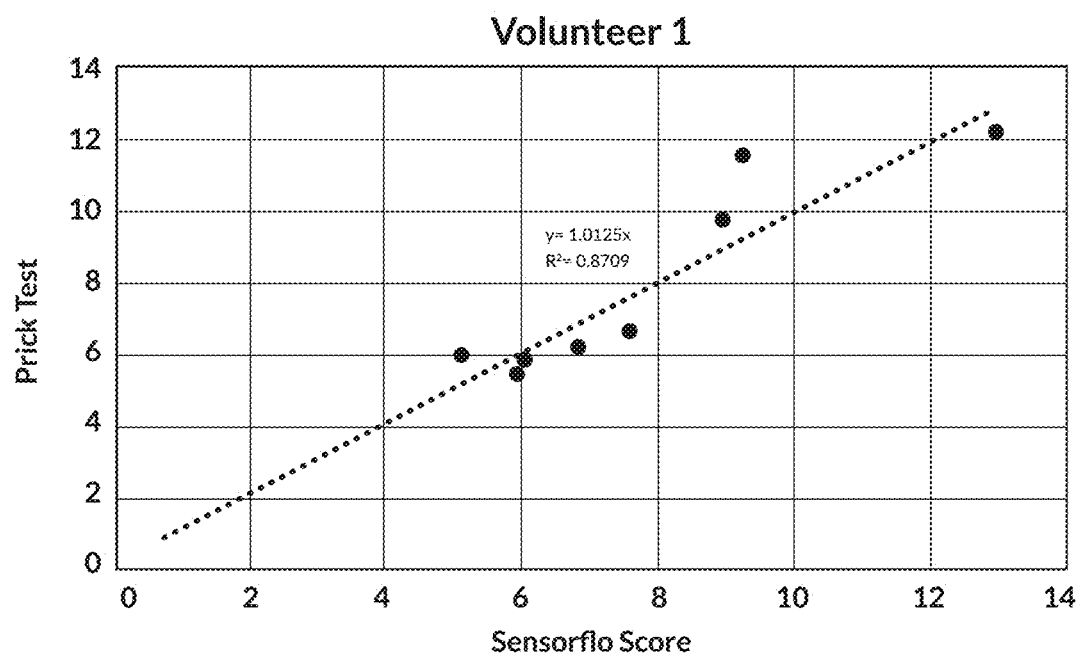

FIG. 1: is a view of one possible embodiment of the present invention,

FIG. 2: is a view of the embodiment of FIG. 1, showing transmitted and reflected electromagnetic radiation signals, when the embodiment rests against a skin surface, FIG. 3: is a view showing the field lines of the antennae of the invention, as illustrated in FIGS. 1 and 2, when the embodiment is adjacent to a skin surface, FIG. 4: a schematic view of one possible embodiment of the present invention, FIG. 5: is a view of the embodiment of the invention illustrated in FIG. 1, in use, FIG. 6: is a view of an embodiment of the invention included within a mobile phone, FIG. 7: is a view of an embodiment of the invention in the form of a wearable watch or wrist strap, FIG. 8: is a view showing different possible arrangements of antennae of the invention, FIG. 9: is the spectral profile or graph resulting from the testing of Volunteer 1, and FIG. 10: is an Excel Table showing the conversion of the spectral profile data into recognisable values for the blood glucose levels of Volunteer 1 (as compared to the equivalent prick test results).

DESCRIPTION OF PREFERRED EMBODIMENTS

Having regard to FIGS. 1 to 5 there is shown a non-invasive sensing system for measuring the concentration of blood glucose 23 (shown as dots in FIGS. 2 and 3) within the blood 14 of a human being, the system being generally indicated by arrow 1.

The system 1 includes a support means, generally indicated by arrow 34 (FIG. 4) in the form of a PCB 22, which is adapted to be placed near to (FIG. 3), or against (FIG. 2), a skin surface 4 of the human being—preferably in the region of the inside surface of the wrist 8 (FIG. 5) of the human being.

The PCB 2 is comprised of a non-hydroscopic dielectric material, and may ideally be between 0.1 mm to 5 mm thick, with a preferred thickness of 0.7 mm In an alternative embodiment, and for use in short use applications, the PCB 2 may instead be comprised of a hydroscopic dielectric material.

The system 1 includes a first transmitting antenna 2, mounted on the PCB 22 for transmitting electromagnetic radiation signals 3 into (and through) the skin surface 4 of the human being.

The system also includes a second receiving antenna 5, mounted on the PCB 22, and directly adjacent to the first antenna 2, for receiving the electromagnetic radiation signals 6 that are reflected back to, or towards, the same region or area of skin surface 4 covered by the PCB, due to the transmitted electromagnetic radiation signals 3 having interacted with the glucose molecules 23 within an artery/vein 13 of the human being.

The first antenna 2 and second antenna 5 are commercially available SMD antennas.

The system 1 further includes an analyser in the form of a two-port VNA 15 which is in electrical communication with the first antenna 2 and the second antenna 5 via the co-axial cables 24a,b, ports 25a,b and conductive tracks 26a,b.

In reality, and as someone skilled in the art would know, there would be two conductive tracks to each antennae 2,5, however for simplicity we have only drawn the single tracks 25a,b.

Amongst other things (described later) the VNA is adapted to break down the reflected or returning signals 6 received by the second antenna 5 into spectra or a spectral file (using S parameters).

A VNA with more than two ports may also be used.

The system further includes a data processor 21 which is adapted to receive the spectra or spectral file from the VNA 15, and turn the reading into a measurement of the concentration of the blood glucose 23 within the blood 14 of an artery/vein 13 of the human being that is undergoing the testing.

The first antenna 2 and receiving antenna 5 are directly adjacent to each other and in substantially the same plane.

Having regard to FIG. 1, it may be seen that the longitudinal axis 27 of the first antenna 2 is substantially orthogonal to the longitudinal axis 28 of the second antenna 5. Hence, the polarity of the first antenna is substantially orthogonal to the polarity of the second antenna. This arrangement is preferred because it minimises the coupling or interference between the first antenna 2 and the second antenna 5. Moreover, having the second (receiving) antenna 5 substantially at right angles to the first (transmitting) antenna 2 means that the second antenna 5 is better disposed to pick up or receive the reflected signals 6, due the change(s) in phase and/or rotation and/or attenuation that the transmitted waves 3 have undergone due to having been reflected (at points 39—FIG. 2).

Moreover, it may be seen that the (central) longitudinal axis 28 of the second antenna 5 passes substantially through the midpoint 29 of the first antenna 2. This is the preferred arrangement of the first antenna 2 with respect to the second antenna 5.

The ports 24a,b of the VNA may be interchanged whereby the second antenna 5 becomes the transmitting antenna and the second antenna 2 becomes the receiving antenna. In such an embodiment, it may be appreciated that the (central) longitudinal axis 28 of the second antenna 5 (now the transmitting antenna) nonetheless still passes substantially through the midpoint 29 of the longitudinal axis 27 of the first antenna 2 (now the receiving antenna).

Having regard to FIG. 1 (in which the various components and distances are not drawn to scale) the distance "a" is approx 5 mm, the distance "b" is approx 6 mm, and the distance "c" is approx 2 mm.

The first conductive track 26a for electrically connecting the VNA 15 to the first antenna 2 is substantially orthogonal to the second conductive track 26b for electrically connecting the VNA 15 to the second antenna 5. This arrangement is preferred because it minimises the coupling or interference between the first and second conductive tracks 26a and 26b.

Having the antennae 2, 5 in a substantially orthogonal relationship combined with the substantially orthogonal relationship of the first and second conductive tracks 26a and 26b combine to greatly minimise (at the least) or completely nullify (at best) the coupling or interference between the first and second conductive tracks 26a and 26b and/or the coupling or interference between the first and second antennae 2, 5.

Having regard to FIGS. 3 and 4, it may be seen that the first antenna 2 and the second antenna 5 protrude slightly from the surface of the PCB 22.

In FIG. 3, the PCB 22, together with the first antenna 2 and second antenna 5 are held just above the skin surface 4. The near field lines 30 are those generated by the electromagnetic signals transmitted by the first antenna 2, and the near field lines 31 are those received by the second antenna 5, after the electromagnetic signals associated with the field lines 30 have been reflected off the blood glucose molecules 23 and/or the bottom 32 of the artery 13.

In FIG. 2, the PCB 22 is placed against the skin surface 4, wherein the first antenna 2 and second antenna 5 are in direct contact with the skin surface 4. This is the preferred arrangement when using the sensing system 1 for this purpose.

In FIG. 2, it may be appreciated that the reflected signals 6 are received by the second antenna 5 in substantially the same place, and on the same side of the skin surface 4 (of the wrist 8), as where the transmitted radiation signals 3 were originally transmitted into the skin 4 by the first antenna 2.

The first transmitting antenna 2 transmits rapidly pulsed electromagnetic radiation signals 3 in the form of a broadband (wide frequency) low power signal.

More specifically, the first antenna 2 transmits electromagnetic radiation signals 3 in the form of continuous waves, with frequencies of between 4 Mhz to 4 Ghz, and a power signal of less than 2 mW.

Both the first antenna 2 and the second antenna 5 are approximately 0.18 cm$^2$, and hence this results in a power density of approximately 11 mW/cm$^2$.

The transmitted signals 3 generally penetrate up to approximately 10 mm within the skin 4, and/or underlying tissue of the human being, before being absorbed by the skin 4 (or underlying tissue).

Having regard to FIG. 2, it may be seen that a portion 33 of the transmitted signals 3 simply pass right through the artery 13, where they are absorbed by the underlying tissue (that is the signal portions 33 are not reflected back to the second antenna 5).

In most (but not all) cases the points 39 where the transmitted signals 3 are reflected back as the reflected signals 6 will generally be between 1 to 5 mm below the skin surface 4.

At the points 39 where the transmitted signals 3 are reflected back as the reflected signals 6 they are rotated in phase prior to being received by the second antenna 5.

Furthermore, the reflected signals 6 also undergo a phase change and a change in attenuation due to having interacted with the glucose molecules 23. It is these changes in dielectric effects that are measured by the VNA 15 in order to produce the spectral file, which is ultimately turned into a blood glucose reading by the data processor 21.

Coupling is increased 100× between the first antenna 2 and the second antenna 5, when the antennae 2, 5 are in contact with the skin 4 (FIG. 2)—as compared to when the first antenna 2 and the second antenna 5 (and/or the PCB 22) are held just above the skin 4 (FIG. 3). This gives rise to absorption or resonant lines or curves in the scans of $S_{11}$ and $S_{22}$ by the VNA 15. $S_{12}$ and $S_{21}$ convey the coupling levels. The scans of $S_{11}$, $S_{21}$, $S_{12}$ and $S_{22}$ are recorded and/or analysed by the VNA and reduced to spectra or a spectral file, and subsequently transmitted to the data processor 21 where they are turned into a recognisable blood glucose concentration (in mml/l) by the data processor 21.

Referring now to known science, when electromagnetic radiation signals travel between two antennae (a "transmitter" and a "receiver") stable electro-magnetic fields are established. Furthermore, the properties of these fields and field lines may be measured. It should be noted that the field needs only to be stable for the period of time that the measurements are being taken, thus high speed pulsed fields and/or "Time of Flight" chirps of only a few wavelengths duration may be considered stable if very high speed signal capturing circuits are used. Devices exist that can generate a pulse/chirp (short electromagnetic pulse) at very specific frequencies. Devices also exist that are able to very rapidly generate through a series of chirps at different frequencies, establish a stable field, capture the signal and measure the field's parameters. The data output of such devices may be referred to as a spectrum. A spectrum of a few hundred discrete data points (frequency steps) can be captured within several milliseconds.

The electromagnetic field can be characterised using several techniques, including but not limited to: "S Parameters ($S_{11}$, $S_{12}$, $S_{21}$, and $S_{22}$), Transmission Line Parameters (Power Loss, Phase angle, RGLC) and dielectric parameters ($\Sigma_r$, $\Sigma_r'$, $\Sigma_r''$). These data may be further analysed to discern properties of the antennae, the waves themselves and the materials that the waves have interacted with.

Electromagnetic radiation signals interact with materials in several ways.

For example, the electromagnetic radiation signals may be reflected (e.g. a mirror and radar), diffracted, refracted (e.g. light prism), speed altered (resulting in phase changes along the wave path), partially or completely absorbed or polarised. Further, the degree of these impacts generally changes with frequency and are specific to the material being interacted with. Each of these interactions impact the electromagnetic radiation signals differently and may therefore be inferred from the wave characteristics. These interactions may be described as dielectric parameters and modelled mathematically using the field parameters.

The received signal may be attenuated but not necessarily. For example, in a perfect signal a reflected wave is 180 degrees out of phase but has not been attenuated. A prism will refract (light) into different wavelengths (or in microwave terms into different frequencies) but again there is no loss or attenuation.

Dielectric Parameters are mathematical terms that describe the effect of the material (eg, blood) on the wave. In homogeneous and stable materials (like plastics and water) these values are very consistent. The terms will typically tell the model the phase change and attenuation per unit of distance that the wave travels in the material (media). These terms may include (a) Phase and attenuation at different frequencies, (b) Real and Imaginary vectors (c) $E_r$, $E'_r$, $E_r''$. From these other parameters can be determined such as (d) RGLC (which are used in an equation involving frequency to get the values for (a) and (b)), also (e) α and β which describe attenuation and phase losses per unit length in a material at any frequency. Transfer functions may be used to convert between some models and their related parameters. For example the S parameters can be converted in $E_r$ parameters using mathematics involving complex numbers.

Field parameters (or field shape parameters) are descriptive of the geometric shape of the field. The field parameter may determine what the mathematical model used (and the complexity and degree of difficulty to solve).

When an electromagnetic radiation signal passes through biological fluids (for example blood, urine, saliva, fruit juice etc) the signals may interact with the fluid in several ways:

Salt ions and polar molecules are driven by the electrical and magnetic fields and migrate to the regions with the opposite charge. The ions absorb some of the wave's energy as they accelerate towards the pole or decelerate if they are moving in the opposite direction to the force. However, in an electromagnetic field the regions of charge are constantly changing poles rapidly, causing the ions to constantly accelerate, decelerate and change directions and absorb energy in proportion to the moment of inertia that has to be overcome. This effect is most prominent at low frequencies and when the ions and molecules are larger and/or highly charged.

Water and polar molecules may also be driven to align with the fields by rotating about their centre of mass and absorb energy as they build up (lose) inertia during acceleration (deceleration). This effect is most prominent in the microwave region.

Biological compounds (whether polar or non-polar) may also have bonds and structures that resonate, flex or otherwise distort at specific frequencies or angles of incidence.

All materials change the speed of the wave and therefore impart phase changes.

Such techniques work best on polar molecules but detection only requires an impacts (e.g. absorption(s), attenuation(s), phase change(s) etc.) that are characteristic of a molecule. For example, benzene is a non-polar molecule but it behaves in a particular way in an electromagnetic field (due to the ring structure and the electron distribution). Also ice and water behave very differently (as ice molecules cannot rotate).

Referring once again to the drawings, and most specifically to FIG. 4, the VNA 15 includes a signal processing unit 9 (SPU).

One function of the SPU 9 is to facilitate the transmission of the electromagnetic radiation signals 3 by the first antenna 2. This is facilitated by the SPU 9 being in electrical communication with a signal generator 10, which in turn is in electrical communication with the first antenna 2.

Another function of the SPU 9 is to receive (or facilitate the receipt of) the reflected radiation signals 6. To accomplish this, there is a signal receiver 11 which is in electrical communication with both the second antenna 5 and the SPU 9. The transflected or reflected electromagnetic radiation signals 6 which are received initially by the second antenna 5, are subsequently transmitted to the signal receiver 11, which in turns transmits them to the SPU 9.

The received signal 6 is analysed in the SPU 9 by initially digitising the received signal 6, and then breaking the digitised signal 6 down into spectra or a spectral file.

Alternatively, examples of other possible ways to break the signal 6 down into spectra, or a spectral file, include power loss and phase and time of flight.

The spectra, or spectral file, is subsequently passed to the data processor 21 and converted into dielectric properties (such as phase angle, power loss; alpha and beta values; $\Sigma r$, $\Sigma r'$ and $\Sigma r''$) and analysed spectrally using chemometric methods, such as and for example, N-PLS, PCA, Neural network Analysis, radio signal processing methods (preferably), Time of Flight Fourier transform) to resolve the component of interest.

The data processor 21 also includes appropriate algorithms, which, when applied to the component of interest (of the spectra or spectral file) ultimately allow the person's blood glucose levels to be determined. A specific example of the type of calculations involved will be described later.

It is envisaged that VNA circuits could be built into the back of the antennae 2,5 if we were looking at miniaturising the system 1.

Attenuation is the loss of energy measured by comparing the energy of the transmitted radiation signals 3 (Po) with the energy of the received radiation signals 6 (P). Attenuation=P/Po (usually reported in dB)

So, in order to "confine the field" we can reduce the energy of the transmitted radiation signals 3 (generally by inserting an attenuator in the circuit between the signal generator 10 and the first antenna 2) so that it cannot penetrate as far into the wrist 8 (attenuation is proportional to the natural log of the distance travelled—so we can calculate the power needed accurately once we know a, or empirically by trying different strength attenuators until we get the desired effect).

Hence, if we set the strength of the transmitted signals 3 so that the near field lines only pass through the skin 4 and blood 14 (i.e. closest to the first antenna 2 and second antenna 5) we will have the strength of signal 6 at the receiving second antenna 5 to be measured, and any radiation signals 33 entering the tissue (behind the artery/vein 13) will be too weak and should be fully absorbed (or transmitted entirely through the wrist 8). In reality, and preferably, we optimise the signals to give us enough signal strength to achieve a usable signal to noise ratio while minimising the "noise" of the tissue. We cannot do much about the skin 4 as we have to go through that and so we make that as "constant" as possible.

If a person had a significant layer of fat tissue beneath their skin, through which the transmitted electromagnetic signals 3 had to first pass through prior to interacting with the artery/vein 13, then we could increase the power level, as required. That is, increasing the power signal to more than 2 mW (which was the example given previously) so that the transmitted electromagnetic signals 3 have enough power to pass through the significant layer of fat, prior to interacting with the artery/vein 13, and subsequently returning as reflected electromagnetic signals 6.

The electromagnetic radiation signals 3 which are transmitted into the wrist 8, and the electromagnetic signals 6 that are received from the wrist 8, may describe or follow a transflectance-type arrangement or pattern, within the electromagnetic field that has been created.

The data processor 21 (or ECM 12) includes (or is in communication with) a wireless communication means in the form of a wireless transceiver 16 for the transmission (and/or receipt) of any or all measurements or other data, or any workings on the measurements or other data, to a remote location or computing device.

In this instance, the wireless transceiver 16 is adapted to send its transmissions to the smartphone 17 of the person being tested. The smartphone 17 includes a downloaded app unique to the system 1 for receiving and/or manipulating and/or displaying the measurements, or other received data, or any workings on the measurements or other data.

The smartphone 17 includes an alarm 18, in this case an audible alarm associated with the smartphone 17—to which the data processor 21 or ECM 12 is programmed to send an appropriate signal (via the transceiver 16) if a predetermined condition is met (for example, the person's blood glucose levels were dangerously low or high and/or that a shot of insulin was required).

It is also envisaged that a text or email could additionally or alternatively be generated to be sent.

Moreover, the data processor 21 or ECM 12 may also be adapted to wirelessly transmit (via the transceiver 16) the measurements, and/or any other data or alarm warnings, to the person's health care professional 19 or to a cloud computing system 20.

In an alternative embodiment, a PIC chip, cellular chip and/or alarm could be put on the same circuit board in the VNA.

The data processor 21 or ECM 12 may be configured to cause the wireless transceiver 16 to transmit and/or receive measurements or other data to/from the person's smartphone 17 or cloud computing system as or when required or desired. The transmissions may be made in real time, manually or at predetermined set times.

In some embodiments, the system 1 or ECM 12 may be configured to receive data or information from the person's smartphone 17 (or cloud computing system 20). For example, software updates for the ECM 12 or data processor 21 or VNA 15 may be transmitted in this way.

Preferably, the smart phone 17 may also be configured to transfer the measurements or other data obtained from the system 1 to a web services platform (not shown).

Preferably, the system may include a memory (not shown) for the storage of the measurements or other data, or any workings on the measurements or other data-. Preferably, the memory may be stored in the ECM 12, data processor 15 and/or smartphones 17.

In some embodiments, a volatile type computer memory, including RAM, DRAM, SRAM, may be used. In such instances, the system may continually transmit the measurements or other data to the smartphone 17 or medical professional 19 or cloud computing system 20.

In other embodiments non-volatile memory formats may be used, including ROM, EEPROM, flash memory, ferroelectric RAM (F-RAM), optical and magnetic computer memory storage devices.

The system 1 may further include a user interface, preferably as part of the smartphone app.

The user interface may also be used to access measurements or other data recorded or received/transmitted by the system 1, and also change any settings of the system 1 (for example, date/time, visual/audio alert settings).

The user interface may also be used to access any measurements or other data received (or transmitted) by the system 1 or to control the upload of the measurements or other data.

In one embodiment, the system 1 may be able or adapted to operate automatically and/or continuously. For example, the system 1 may be configured to automatically take a measurement every hour, 24 hours a day.

In another embodiment, the system 1 may be able, or adapted, to operate automatically and (more-or-less) continuously. For example, the system 1 may be configured to automatically take a measurement every second or every minute, 24 hours a day.

Alternatively, and/or additionally, the system 1 may be able or adapted to be operated manually. For example, a person may place the PCB 22 on the inside of their wrist 8 and manually take a reading, for example by engaging an "on" button associated with the system 1 (or smartphone app).

In the embodiments shown, the support means 34, VNA 15, data processor 21 and transceiver 16 (collectively referred to herein as "the componentry") may be housed within its own housing (not shown) which, for example, may be carried by a person. As such, the person's smartphone 17 (and associated app) may be adapted, or able to operate, or be in communication with, the componentry. Hence, the componentry and the app combine to operate the system 1 or facilitate the operation of the system 1.

FIG. 5 illustrates how the embodiment illustrated in FIG. 1 may be used in practice. A person who wishes to take a blood glucose reading places the PCB 22 against an inside surface of their wrist 8, as shown. It is envisaged however that the PCB 22 could be placed against any skin surface, for example the neck, the leg, foot or chest. However, the wrist is a preferred place given that it has at least one artery 13 close to the skin surface 4.

The PCB 22 is connected to the VNA 15, which in turn is connected to a data processor in the form of a laptop 37.

Preferably, the PCB 22 should be placed upon the wrist 8, wherein the longitudinal axis of the first antenna 2 or the longitudinal axis of the second antenna 5 line up substantially with the longitudinal axis 38 of at least one artery 13, as this allows for greater accuracy in the blood glucose readings (as compared to the PCB 22 being placed on the wrist 8, wherein the longitudinal axes 27, 28 of the antennae 2, 5 are both at an angle with respect to the longitudinal axis 38 of at least one artery 13).

Having regard to FIG. 6, the first antenna 2 and the second antenna 5 are housed within or upon a mobile phone 35. The mobile phone 35 may also incorporate a miniaturised VNA and/or data processor (not shown). That is, the mobile phone 35 may incorporate a miniaturised version of the system 1 as a whole—which may subsequently transmit the resultant blood glucose reading to an app associated with the smartphone 35 (as described previously with respect to FIG. 4).

Having regard to FIG. 7, the first antenna 2 and the second antenna 5 are housed within or upon a wearable wrist or watch strap 36.

It is also envisaged that the first and second antennae 2, 5 may instead be housed within the body 40 of the watch itself, and preferably on the underside 41 of the watch body 40, whereby the first and second antennae 2,5 are in direct contact with the skin 4 of the person in the region of the wrist 8 (topside or underside). It may be appreciated that if worn by a human being (next to the skin 4) the system 1 may be able to continuously detect for the presence of, or measure the concentration of, or otherwise monitor, blood glucose 23 within the blood 14—this has advantages as compared to discreet finger prick tests which only take measurements each time the person manually pricks their finger and places the resultant blood on/in a glucose meter. Moreover, being able to continuously wear the watch 40 or strap 36 means that a person is able to continuously monitor their blood glucose levels whilst working, exercising, socialising or sleeping.

The wearable wrist or watch strap 36 may also incorporate a miniaturised VNA and/or data processor (not shown) whereby the strap 36 may be seen to incorporate a miniaturised version of the system 1, as a whole. In such an embodiment, the strap 36 or watch 40 may include a wireless transceiver (not shown) whereby the resultant blood glucose reading may be wirelessly transmitted to another electronic device, as described previously.

Having regard to FIG. 8, there are shown in FIGS. 8a, 8b, 8c, and 8d four different possible configurations, and number, of first and second antennae 2, 5 that may be housed by, or within, the support means 34, such as the PCB 22.

In FIG. 8a, there is one transmitting antenna 2 and one receiving antenna 5, arranged substantially parallel, and side to side.

In FIG. 8b, there is one transmitting antenna 2 and one receiving antenna 5, arranged substantially parallel, and end to end.

In FIG. 8c, there is one transmitting antenna 2, positioned substantially orthogonally to two substantially parallel receiving antennae 5, positioned on each side of the first transmitting antenna 2.

In FIG. 8d, there are three transmitting antennae 2 positioned substantially orthogonally to two substantially parallel receiving antennae 5, positioned as shown.

The system 1 has been tested and the results compared to the results of a standard prick test. The parameters of the test undertaken on a volunteer ("Volunteer 1") are outlined below:

Methodology
1. On the day before the testing day, Volunteer 1 had their "personal profile" traced (using acetate film on the computer screen) and then practised moving their arm to consistently obtain a trace matching their "personal profile".
2. On the testing day, Volunteer 1 was monitored for a period of up to two (2) hours. They were required to stay at the trial facilities for the period of their monitoring.
3. On the morning of the testing day, Volunteer 1 was required to have their blood glucose level between 5-7 mmoll$^{-1}$ prior to starting the monitoring. This required Volunteer 1 foregoing food leading up to the trial period.
4. During the monitoring period.
    a. Prior to eating Volunteer 1 was required to do two prick tests (within a few minutes of each other). The results of the prick test were recorded (as the baseline)
    b. Volunteer 1 was given a moderate amount of GI food (a sandwich)
    c. Immediately, and then every five minutes after, Volunteer 1:
        Placed the sensor 1 (or PCB 22) on their arm so that the trace was over their "personal profile" and had a measurement taken and saved.
        Did a prick test
    d. The prick test results were monitored by a medical supervisor to ensure that Volunteer 1 never had excessively low or high blood glucose levels.
    e. Once Volunteer 1's glucose level reached 12-14 mmol·l$^{-1}$ (or the prick test stabilised) Volunteer 1 was excused from the trial.

A spectral profile in the form of a graph showing the results of the testing of Volunteer 1 is marked as FIG. 9.

FIG. 10 is an Excel Table showing the conversion of the spectral profile data into recognisable values for the blood glucose levels of Volunteer 1 (as compared to the equivalent prick test results). The formula used for the conversion is also provided.

As can be seen from FIG. 10, the test results on Volunteer 1 using the system 1 are mostly very close to the equivalent prick test results (keeping in mind that prick test results can be up to 15% different to actual—as compared to more accurate laboratory testing methods).

Variations

While the embodiments described above are currently preferred, it will be appreciated that a wide range of other variations might also be made within the general spirit and scope of the invention, and/or as defined by the appended claims.

We claim:
1. A non-invasive sensing system for measuring the concentration of a substance within an object, said system comprising:
    a support configured to be placed near to, or against, a surface of the object;
    a transmitting antenna mounted upon or within the support, the transmitting antenna configured to transmit electromagnetic radiation signals into the object; and
    a receiving antenna mounted upon or within the support, and adjacent to the transmitting antenna, the receiving antenna configured to receive at least a portion of the electromagnetic radiation signals that are reflected back to the same surface of the object covered by the support, due to the transmitted electromagnetic radiation signals having interacted with the substance within the object being measured,
    wherein the central longitudinal axis of the transmitting antenna is substantially orthogonal to the central longitudinal axis of the receiving antenna,
    the central longitudinal axis of the receiving antenna passes substantially through the center of the transmitting antenna, or the central longitudinal axis of the transmitting antenna passes substantially through the center of the receiving antenna, and
    the transmitting antenna and the receiving antenna lie in substantially the same plane with respect to each other.
2. The non-invasive sensing system for measuring the concentration of the substance within the object, as claimed in claim 1, further comprising an analyzer which is in electrical communication with the transmitting antenna and the receiving antenna, the analyzer being configured to break down a reflected signal received by the receiving antenna into spectra or a spectral file.
3. The non-invasive sensing system for measuring the concentration of the substance within the object, as claimed in claim 2, further comprising a data processor configured to receive the spectra or spectral file from the analyzer, and measure a concentration of the substance within the object.
4. The non-invasive sensing system for measuring the concentration of the substance within the object, as claimed in claim 2, wherein the support includes at least one first conductive track configured to electrically connect the analyzer to the transmitting antenna, and at least one second conductive track configured to electrically connect the analyzer to the receiving antenna, the at least one first conductive track being substantially orthogonal to the at least one second conductive track.
5. The non-invasive sensing system for measuring the concentration of the substance within the object, as claimed in claim 2, wherein the analyzer is a vector network analyzer

(VNA), and the VNA uses S parameters to break down the received signal from the second receiving antenna into spectra or a spectral file.

6. The non-invasive sensing system for measuring the concentration of the substance within the object, as claimed in claim 2, further comprising an electronics control module (ECM) the configured to control an overall operation of one or more of the sensing system, the analyzer, and a data processor.

7. The non-invasive sensing system for measuring the concentration of the substance within the object, as claimed in claim 1, wherein the first transmitting antenna and the second receiving antenna are configured to be in direct contact with the surface of the object.

8. The non-invasive sensing system for measuring the concentration of the substance within the object, as claimed in claim 7, wherein the support is configured to be worn by a human being.

9. The non-invasive sensing system for measuring the concentration of the substance within the object, as claimed in claim 1, wherein the non-invasive sensing system is configured to measure the concentration of the substance that is a blood component within the blood of a body of a living being.

10. The non-invasive sensing system for measuring the concentration of the substance within the object, as claimed in claim 1, wherein the transmitted electromagnetic radiation signals are in one or more of the microwave spectrum and the radio wave spectrum.

11. The non-invasive sensing system for measuring the concentration of the substance within the object, as claimed in claim 1, wherein the transmitted electromagnetic radiation signals are transmitted continuously.

12. The non-invasive sensing system for measuring the concentration of the substance within the object, as claimed in claim 1, wherein the transmitted electromagnetic radiation signals are transmitted in pulses or chirps.

13. The non-invasive sensing system for measuring the concentration of the substance within the object, as claimed in claim 1, wherein the power of the transmitted electromagnetic radiation signals is below 50 mW.

14. The non-invasive sensing system for measuring the concentration of the substance within the object, as claimed in claim 1, wherein the first transmitting antenna is between 0.05 mm-10 mm away from the second receiving antenna.

15. The non-invasive sensing system for measuring the concentration of the substance within the object, as claimed in claim 1, wherein the transmitting antenna is configured to transmit the electromagnetic radiation signals into the object with a transflectance-type arrangement or pattern, and the receiving antenna is configured to receive the electromagnetic radiation signals that are reflected back with the transflectance-type arrangement or pattern.

16. The non-invasive sensing system for measuring the concentration of the substance within the object, as claimed in claim 1, wherein the support includes a printed circuit board (PCB).

17. The non-invasive sensing system for measuring the concentration of the substance within the object, as claimed in claim 1, wherein the system is able, or configured, to operate automatically at predetermined times.

18. The non-invasive sensing system for measuring the concentration of the substance within the object, as claimed in claim 1, wherein the system is able, or configured, to operate automatically and continuously.

19. The non-invasive sensing system for measuring the concentration of the substance within the object, as claimed in claim 1, wherein the system is able, or configured, to be operated manually by a user of the system.

20. The non-invasive sensing system for measuring the concentration of the substance within the object, as claimed in claim 1, wherein the system is able to measure the concentrations of a plurality of substances at any one time.

21. The non-invasive sensing system for measuring the concentration of the substance within the object, as claimed in claim 1, wherein the support is in the form of, or includes, a housing or substrate.

22. A non-invasive sensing system for measuring the concentration of a substance within an object, said system comprising:
    a support configured to be placed near to, or against, a surface of the object;
    at least one transmitting antenna mounted upon or within the support, the at least one transmitting antenna configured to transmit electromagnetic radiation signals into the object; and
    at least one receiving antenna mounted upon or within the support, and adjacent to the transmitting antenna, the at least one receiving antenna configured to receive at least a portion of the electromagnetic radiation signals that are reflected back to the same surface of the object covered by the support, due to the transmitted electromagnetic radiation signals having interacted with the substance within the object being measured,
    wherein the central longitudinal axis of the at least one transmitting antenna is substantially orthogonal to the central longitudinal axis of the at least one receiving antenna,
    the central longitudinal axis of the at least one receiving antenna passes substantially through a midpoint of the at least one transmitting antenna, or the central longitudinal axis of the at least one transmitting antenna passes substantially through a midpoint of the at least one receiving antenna, and
    the at least one transmitting antenna and the at least one receiving antenna lie in substantially the same plane with respect to each other.

* * * * *